United States Patent
Pelgrim et al.

(10) Patent No.: US 8,617,044 B2
(45) Date of Patent: Dec. 31, 2013

(54) STRESS REDUCTION

(75) Inventors: Petronella Hendrika Pelgrim, Eindhoven (NL); Evert Jan Van Loenen, Eindhoven (NL); Frank Wartena, Eindhoven (NL); Joanne Henriette Desiree Monique Westerink, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1241 days.

(21) Appl. No.: 12/517,853

(22) PCT Filed: Dec. 5, 2007

(86) PCT No.: PCT/IB2007/054931
§ 371 (c)(1), (2), (4) Date: Jun. 5, 2009

(87) PCT Pub. No.: WO2008/072137
PCT Pub. Date: Jun. 19, 2008

(65) Prior Publication Data
US 2010/0331607 A1    Dec. 30, 2010

(30) Foreign Application Priority Data
Dec. 12, 2006   (EP) .................................... 06125869

(51) Int. Cl.
*A61M 21/00*    (2006.01)

(52) U.S. Cl.
USPC ............................................................ 600/26

(58) Field of Classification Search
USPC .................................................... 600/26–28
See application file for complete search history.

(56) References Cited

U.S. PATENT DOCUMENTS

| | | | |
|---|---|---|---|
| 5,304,112 A * | 4/1994 | Mrklas et al. .................. 600/27 |
| 5,465,729 A | 11/1995 | Bittman | |
| 6,102,846 A | 8/2000 | Patton | |
| 6,484,062 B1 | 11/2002 | Kim | |
| 6,527,700 B1 * | 3/2003 | Manico et al. .................. 600/26 |

FOREIGN PATENT DOCUMENTS

| | | |
|---|---|---|
| EP | 0938866 A1 | 9/1999 |
| JP | 2000298530 A | 10/2000 |
| JP | 2000357022 A | 12/2000 |
| WO | 9851286 A1 | 11/1998 |

* cited by examiner

*Primary Examiner* — John Lacyk

(57) ABSTRACT

A method and system for reducing stress in a working environment. In a conditioning phase a positive association of a sensory stimulus, such as a scent, image and/or sound with a relaxed feeling is created. Following the creation of this positive association the "relaxing" stimulus will be used as a de-stressor in the usage phase. That is, when it is detected that the user is stressed, the "relaxing" stimulus is released to reduce stress.

17 Claims, 3 Drawing Sheets

STRESS REDUCTION

BACKGROUND OF THE INVENTION

1. Technical Field

The present invention relates to a method, software and a system for reducing stress.

2. Description of Related Art

Several surveys show that many people suffer from stress at work. For example, a survey by Northwestern National Life indicates that 40% of workers report that their job is very or extremely stressful. A survey by Yale University indicates that 29% of workers report that they feel quite a bit or extremely stressed at work. It has been reported that high stress yearly generates a cost of $136 per employee, making stress very expensive for employers.

According to the National Institute for Occupational Safety and Health (NIOSH, see, the Internet, cdc.gov/niosh/stresswk.html), job stress can be defined as the harmful physical and emotional responses that occur when the requirements of the job do not match the capabilities, resources, or needs of the worker. Job stress can lead to poor health and even injury.

The potential effects of stimuli, such as scents, images and sounds to reduce stress levels have been demonstrated. Studies suggest that this effect is strongly linked to somatic markers, which are stored in memory. These somatic markers trigger bodily sensations that accompany emotion. Music (and probably also scent and images) reinforces this process and thereby enhances naturally occurring bodily responses.

The U.S. Pat. No. 6,102,846 discloses an apparatus and method for managing a psychological and physiological state of an individual involving the use of images or stimuli, the measurement of a physiological state of the individual, and the creation of a personalized preferred response profile which is specifically tailored to the individual. With the apparatus and method disclosed, it is possible for an individual to manage and thereby lower his or her stress by viewing, for example, images which are selected based on the created personalized preferred response profile for the individual. The personalized preferred response profile is created by having the individual view, for example, a wide variety of images, and creating the profile based on those images which provide a preferred response to the individual.

It is an object of the invention to provide an improved method and system to reduce stress, in particular mental fatigue, which is effective and easy to implement.

SUMMARY OF THE INVENTION

This and other objects of the invention are achieved by a method according to claim 1, a computer program according to claim 14 and a system according to claim 17. Favorable embodiments are defined by the dependent claims 2-13 and 15-16.

According to an aspect of the invention a method is provided for reducing stress of a user. In a conditioning phase, the user is repeatedly provided with at least a sensory stimulus, when he/she is relaxed. In a subsequent usage phase, it is detected if the user is stressed. If this is the case, the user is provided with the same stimulus, which in the earlier conditioning phase was provided to the user when he/she was relaxed.

In the conditioning phase a positive association of the stimulus with a relaxed feeling is created. Following the creation of this positive association the "relaxing" stimulus will be used as a de-stressor in the usage phase. That is, when the user is stressed, the "relaxing" stimulus is released to reduce stress. This is possible due to the initial pairing of the stimulus with the situation that makes the user feel relaxed. The result is that the stimulus will be able to evoke the relaxed feeling by itself and will have a positive effect on the user. This associative learning is called Pavlovian conditioning.

The method according to the invention is preferably used for workers on computers in an office environment. However, it may also be implemented in other working environments where stress or mental fatigue of workers exists, such as an assembly line. In some assembly lines the noise and smell might interfere with the stimulus and therefore this needs to be taken into account, for instance by using head phones. The method promotes healthy and productive working, by reducing cognitive load, reducing muscle tension and evoking a pleasant emotion.

In the conditioning phase, the user may indicate that he/she is relaxed, whereupon he/she is provided with the stimulus. However, it is preferred that the relaxed condition is detected automatically. In this way, the need of active participation of the user is avoided.

Preferably, the stimulus is taken from the group of scents, sounds and images, which are previously evaluated as pleasant by the user. Several studies have demonstrated the potential effects of scents, images and sounds, such as music to reduce stress levels.

According to a further embodiment the user is enabled to set preferences regarding the stimulus to be employed and their type. For example, the user may set that only scents and music are to be used, because he finds the use of images too intrusive for his work. Furthermore, the user may be enabled to select the stimulus to be employed. In this way, the user may select scents (for example lavender), music and/or images that make him/her relaxed.

According to a still further embodiment, the step of detecting that the user is stressed includes: measuring a parameter indicative of the stress of a user; and determining if the user is stressed based on the value of the measured parameter. In this way, a stressful condition of the user is detected in a reliable way.

According to a first alternative of this embodiment the parameter indicative of the stress of the user is the time that has elapsed since the user has started an activity without interruption. When the time exceeds a predefined value it is determined that the user is stressed. A default value for the predefined value can be set according to large scale investigations on averages amongst multiple users. So how long does the average non-stressed person spend continued time working on an activity? This time can be set as the maximum default allotted time for 'undisturbed work' and the system determines that the user is in a stressed condition, when the continued time working exceeds this value.

According to a further embodiment, the parameter indicative of the stress of the user is the number of actions performed by the user during a predetermined time interval. It is determined that the user is stressed when the number exceeds a predefined value. The number of actions performed by the user per time interval may be an indicator of the user's stress or mental fatigue. In case that the user is a worker on a computer system, the actions may be the number of key strokes or mouse clicks per time interval.

Alternatively or additionally, the parameter indicative of the stress of the user is the number of errors made by the user or the number of corrections of errors made by the user during a time interval. It is determined that the user is stressed when the number exceeds a predefined value. In case that the user is a worker on a computer system, the number of corrections of errors may be counted by counting the number of times the Backspace or Delete button has been used, or how many times the user has selected an "Undo" option or typed Ctrl-Z per time interval (e.g. 30 minutes). The underlying assumption is that if a user makes more typing errors than normal, he/she is stressed.

When, as according to these embodiments, the user's keyboard and mouse usage is used to determine if the user is stressed, one should realize that different persons have different usage patterns, even when they are relaxed. For this reason, preferably, a personal pattern is taken into account in the determining step. Thereby, it is avoided that a stress condition of a user is erroneously detected.

This pattern can be built by:

monitoring the person's keyboard and mouse usage for a certain period of time (e.g. weeks), and by asking the person at certain moments whether he feels stressed (e.g. "please indicate your current stress level: no stress—medium stress—high stress").

letting the user type a certain text, and by asking the person whether he feels stressed at this moment (e.g. "please indicate your current stress level: no stress—medium stress—high stress").

By combining the usage data and answers, the stress condition of a user can be determined more accurately.

Alternatively or additionally, the parameter indicative of the stress of the user is a physiological parameter of the user. Some physiological values such as body temperature or Galvanic Skin Response (GSR) may be indicative of mental fatigue of the user. Therefore, they may advantageously be used to determine if the user is stressed or not. This embodiment may be implemented by means of a personal computer or, alternatively by means of a bracelet, which can detect the users stress level from physiological data and emit scents and sounds accordingly.

Preferably, the method according to the invention is implemented by means of a computer program.

According to a further aspect of the invention a system is provided for reducing stress of a user comprising:

providing means for providing the user with at least a stimulus, when the user is relaxed, in a conditioning phase, and detecting means for detecting that the user is stressed, in a usage phase; wherein, if it is detected that the user is stressed, the providing means are adapted for providing the user with the stimulus, which in the earlier conditioning phase was provided to the user, when the user was relaxed.

These and other aspects of the invention will be apparent from and elucidated with reference to the embodiments described hereinafter.

BRIEF DESCRIPTION OF THE DRAWINGS

The invention will be better understood and its numerous objects and advantages will become more apparent to those skilled in the art by reference to the following drawings, in conjunction with the accompanying specification, in which.

Throughout the figures like reference numerals refer to like elements.

DETAILED DESCRIPTION OF THE PRESENT INVENTION

According to the invention a method is provided for reducing stress of a user. It comprises a conditioning phase, wherein a positive association of a sensory stimulus with a relaxed feeling is created. Following the creation of this positive association the "relaxing" stimulus will be used as a de-stressor in stressed situations during a usage phase. Preferably, the method according to the invention is implemented for reducing mental stress of workers on computer systems in an office environment but it may also be used for stress reduction in other working environments, such as assembly lines.

Figure 1:
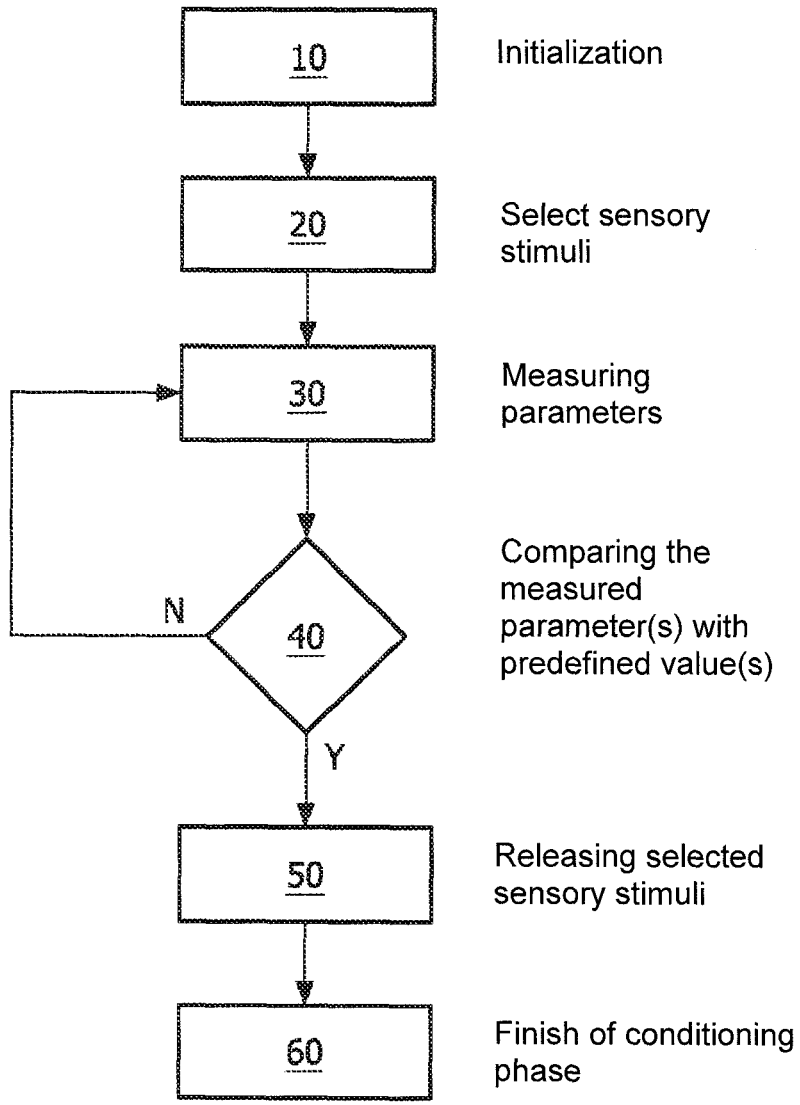
FIG. 1 shows a flow chart of the conditioning phase of the method according to the invention.

FIG. 1 shows a flow chart of the conditioning phase in an exemplary way. After initialization (step 10), the user can set his preferences with regard to which sort of sensory stimuli he/she wants to employ (for example, only scent and music) in step 20. Alternatively or additionally, the user can select the pictures, music and scents (for example, lavender scent), that make him/her relaxed and that he/she finds pleasant (or at least not unpleasant).

Then the user is observed during his/her normal work to detect relaxing or pleasant situations. Preferably, this is done by measuring one or more parameters, which are indicative of a relaxed feeling (step 30) and subsequently comparing the measured parameter(s) with predefined value(s) (step 40). Alternatively, the user can indicate if he is relaxed by means of a user interface. If the user is not relaxed, step 30 is repeated. If the user is determined to be relaxed, in step 50 one or more of the sensory stimuli selected by the user in step 20 are released. Steps 30, 40 and 50 need to be performed several times before the conditioning phase is finished (step 60). In the conditioning phase a positive association between the stimulus/stimuli and the relaxed feeling is created.

Figure 2:
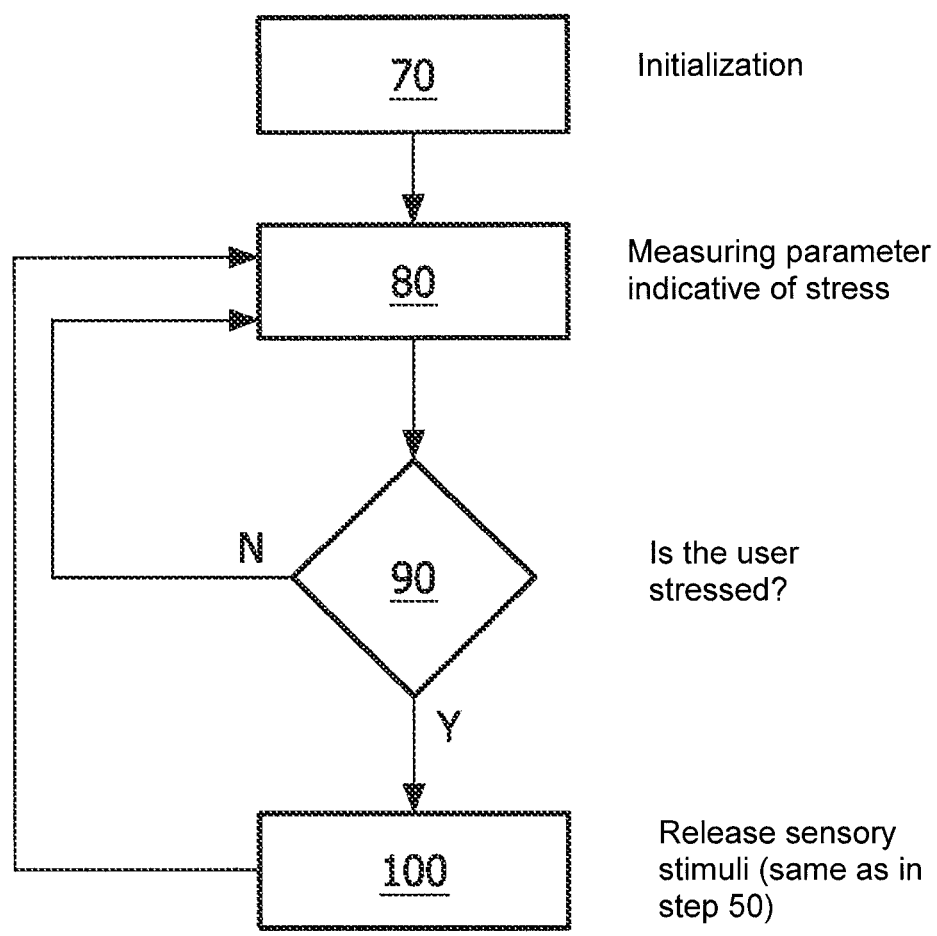
FIG. 2 a flow chart of the usage phase of the method according to the invention.

Later, in the usage phase the stimulus/stimuli is/are used to reduce the user's stress. FIG. 2 shows a flow chart of the usage phase in an exemplary way. After initialization (step 70), a parameter indicative of the stress of the user is measured (step 80). In step 90 it is determined if the user is stressed. This is done by comparing the measured parameter(s) with predefined value(s). If the user is not stressed, step 80 is repeated. If the user is stressed, in step 100 one or more of the sensory stimuli released to the user in step 50 of the conditioning phase are released, again. When the release of the stimulus/stimuli is finished and possibly after a predetermined time-out period, step 80 is repeated.

When focusing on workers using a computer, in the usage phase the user's typing behaviour may be constantly monitored and deviations that indicate stress are used to trigger the onset of several sensory stimuli. The following parameters indicative of stress of a user may be used to detect that the user is stressed:

1. the number of key strokes or mouse clicks per time interval (e.g. 30 minutes) is counted (step 80). When this number exceeds a predefined value (as determined in step 90), the user is determined to be stressed or likely to become stressed. The underlying assumption is that a high number of keystrokes or mouse clicks per time interval is an indication of user stress.

2. the number of times that the Backspace or Delete button has been used, or how many times the user has selected the "Undo Typing" option or typed Ctrl-Z per time unit (e.g. 30 minutes) is counted (step 80). When this number exceeds a predefined value (as determined in step 90), the user is determined to be stressed. The underlying assumption is that if a user makes more typing errors than normal, he is less concentrated, and he/she needs to be provided with a stress reducing stimulus.

3. Time spent on one task (for instance, time spent on typing in a Word document without an interruption of using another application).
4. Number of times the user ignores a "rest break" (e.g. as indicated by the Work Pace program).
5. The time it takes before the user responds to a "rest break" and pauses his/her work (e.g. as indicated by the Work Pace program)

When the user's keyboard and mouse usage is used to determine if the user is stressed, one should realize that different persons have different usage patterns, even when they are relaxed. For this reason, preferably, a personal pattern is taken into account in the determining step 90. So, stress is detected by monitoring the user's typing behaviour and comparing this to his/her normal typing behaviour. Thereby, it is avoided that a stress condition of a user is erroneously detected.

This personal pattern can be built by:
monitoring the person's keyboard and mouse usage for a certain period of time (e.g. weeks), and by asking the person at certain moments whether he feels stressed (e.g. "please indicate your current stress level: no stress—medium stress—high stress").
letting the user type a certain text, and by asking the person whether he feels stressed at this moment (e.g. "please indicate your current stress level: no stress—medium stress—high stress").

By combining the usage data and answers, the stress condition of a user can be determined more accurately.

Alternatively, large scale investigations on averages can be taken into account in the determining step 90. This is advantageous in case that the time spent on one task without an interruption of using another application is used as the parameter indicative of the stress of a user. The time that the average non-stressed person spends continued time working on the computer can be set as the maximum default allotted time for 'undisturbed work'. The system may trigger the release of a stimulus, when the continued time working on the computer exceeds this value.

According to a further alternative, a physiological parameter of a user, which is indicative of stress, is measured, such as the body temperature or GSR (step 80). When the measured parameter has a value indicative of undesirable stress of the user (as determined in step 90), the user is determined to be stressed, and is provided with the stimulus. In case that the physiological parameter is the body temperature, the stimulus could be provided, if the temperature is over a predefined value.

The sensory stimuli released to the user in step 100 may be one or more of scents, sounds or images. If the stimuli are images, they are presented on the computer screen. However, this refrains the user from continuing his/her work (unless he/she decides to abort the application). Releasing scents and playing music are less intrusive. A standard media application can be used to play music. A scent dispenser, which can be connected to the PC, can be used to release scents. The user is in control and can abort the release of the stimulus/stimuli at any time.

In case that the method is used in an assembly line, relaxing sounds may be released to the user by means of head phones, since smell and noise on the assembly line might interfere with the stimulus.

Figure 3:
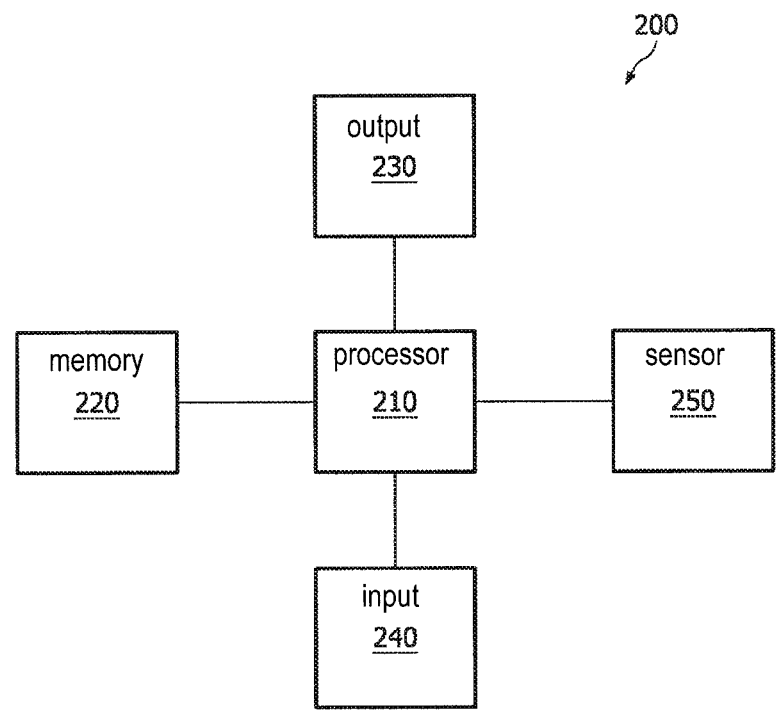
FIG. 3 shows a block diagram of a system for implementing the method according to the invention.

FIG. 3 illustrates a computer system 200 for implementing the method according to FIGS. 1 and 2. It shows a processor 210, a memory 220, an output means 230, such as a display, a loudspeaker and a scent dispenser, an input means 240 (keyboard and mouse), and optionally, measuring means 250 for measuring (a) physiological parameter(s) of a user. The processor 210 executes instructions stored in the memory 220, according to the method of FIG. 1. The output means 230 are used to provide the user with the stimulus/stimuli. The input means 240 and optionally the measuring means 250 are used to obtain information to determine the moment of providing the stimulus/stimuli to the user.

As will be recognized by those skilled in the art, the innovative concepts described in the present application can be modified and varied over a wide range of applications.

Accordingly, the scope of patented subject matter should not be limited to any of the specific exemplary teachings discussed, but is instead defined by the following claims.

Any reference signs in the claims shall not be construed as limiting the scope thereof.

The invention claimed is:

1. A method for reducing stress of a user, the method comprising acts of:
in a conditioning phase when the user is relaxed, repeatedly providing the user with at least a first sensory stimulus;
monitoring a stress level of the user; and
in a usage phase when the user is stressed, providing the user with the first sensory stimulus.

2. The method according to claim 1, wherein the first sensory stimulus is selected from one of scents, sounds and images.

3. The method according to claim 1, wherein the user sets preferences regarding a selection of the first sensory stimulus to be provided.

4. The method according to claim 3, wherein the user selects the first sensory stimulus to be provided.

5. The method according to claim 1, wherein monitoring comprises acts of:
measuring a parameter indicative of the stress of the user;
determining if the value of the measured parameter indicates stress in comparison with a predefined value.

6. The method according to claim 5, wherein in the conditioning phase, the measuring and determining is performed for each repetition of providing the first sensory stimulus.

7. The method according to claim 5, wherein the parameter comprises time that has elapsed since the user has started an activity without interruption.

8. The method according to claim 5, wherein the parameter comprises a number of actions performed by the user during a predetermined time interval.

9. The method according to claim 5, wherein the parameter comprises a number of errors made by the user or the number or corrections of errors made by the user during a time interval.

10. The method according to claim 5, wherein the parameter comprises an analysis of usage of the user's keyboard and mouse.

11. The method according to claim 5, further comprising an act of taking a personal pattern into account in determining stress.

12. The method according to claim 5, wherein the parameter is a physiological parameter of the user.

13. The method according to claim 1, wherein the user is a computer user.

14. A computer program comprising computer readable program code embodied on a non-transitory computer readable medium, when executed on a computer said program performs a method for reducing stress of a user, the method comprising acts of:

in a conditioning phase when the user is relaxed, repeatedly providing the user with at least a first sensory stimulus;

monitoring a stress level of the user; and in a usage phase when the user is stressed, providing the user with the first sensory stimulus.

15. The computer program as claimed in claim 14, wherein the act of monitoring the stress level of the user comprises an act of monitoring at least one of body temperature and Galvanic Skin Response.

16. A computer readable carrier medium embodying non-transitory program code executable on a computer to perform a method for reducing stress of a user, the method comprising acts of:

in a conditioning phase when the user is relaxed, repeatedly providing the user with at least a first sensory stimulus;

monitoring a stress level of the user; and in a usage phase when the user is stressed, providing the user with the first sensory stimulus.

17. A system for reducing stress of a user comprising:

a processor for monitoring a stress level of the user; and a stimulator configured in a conditioning phase when the user is relaxed, to repeatedly provide the user with at least a first sensory stimulus, and in a usage phase when the user is stressed, to provide the user with the first sensory stimulus.

\* \* \* \* \*